United States Patent

Witte et al.

[11] 4,151,303
[45] Apr. 24, 1979

[54] PHENOXYALKYLCARBOXYLIC ACID COMPOUNDS AND SERUM-LIPID AND TRIGLYCERIDE DEPRESSING THERAPEUTIC COMPOSITIONS

[75] Inventors: Ernst-Christian Witte; Hans P. Wolff, both of Mannheim, Fed. Rep. of Germany; Kurt Stach, deceased, late of Mannheim-Waldhof, Fed. Rep. of Germany, by Werner Plattner, Executor; Wolfgang Schaumann, Heidelberg; Karlheinz Stegmeier, Schriesheim, both of Fed. Rep. of Germany

[73] Assignee: Boehringer Mannheim GmbH, Mannheim-Waldhof, Fed. Rep. of Germany

[21] Appl. No.: 719,878

[22] Filed: Sep. 1, 1976

[30] Foreign Application Priority Data

Sep. 17, 1975 [DE] Fed. Rep. of Germany ....... 2541342

[51] Int. Cl.² ...................... C07C 101/42; A01N 9/20
[52] U.S. Cl. .................... 424/319; 424/309; 560/42; 562/451; 260/501.11
[58] Field of Search .......... 260/519, 471 R; 424/308, 319, 309; 560/39, 42; 562/451

[56] References Cited

U.S. PATENT DOCUMENTS

| 3,551,409 | 12/1970 | Kampe et al. | 424/180 |
|---|---|---|---|
| 3,781,328 | 12/1973 | Witte et al. | 260/471 R |
| 4,010,279 | 3/1977 | Griss et al. | 260/471 R |

*Primary Examiner*—James O. Thomas, Jr.
*Assistant Examiner*—James H. Reamer
*Attorney, Agent, or Firm*—Sprung, Felfe, Horn, Lynch & Kramer

[57] ABSTRACT

Novel phenoxyalkylcarboxylic acid compounds of the formula

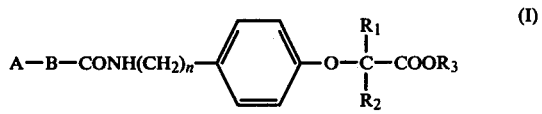

wherein
A is aryl, aryloxy, substituted aryl or substituted aryloxy, wherein the substituents are selected from lower alkyl, lower alkoxy, halogen and haloalkyl;
B is a straight-chained or branched, saturated or unsaturated hydrocarbyl containing up to 5 carbon atoms;
n is 1, 2 or 3 and
$R_1$, $R_2$ and $R_3$, which may be the same or different, are hydrogen or lower alkyl;
and the pharmacologically compatible salts thereof; have been found to be outstandingly effective in depressing serum-lipid and triglycerides in the serum of mammals.

28 Claims, No Drawings

PHENOXYALKYLCARBOXYLIC ACID COMPOUNDS AND SERUM-LIPID AND TRIGLYCERIDE DEPRESSING THERAPEUTIC COMPOSITIONS

The present invention relates to new phenoxyalkylcarboxylic acid compounds. The invention also relates to lipid-depressing compositions containing such compounds and to methods of depressing the serum lipid content in mammals.

The new phenoxyalkylcarboxylic acid derivatives according to the present invention are of the formula:

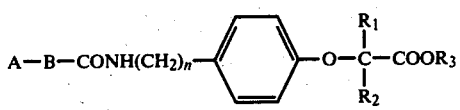

wherein
A is aryl or aryloxy, optionally substituted by lower alkyl or alkoxy radicals, halogen atoms or haloalkyl radicals,
B is a straight-chained or branched, saturated or unsaturated hydrocarbyl containing up to 5 carbon atoms,
n is 1, 2 or 3 and
$R_1$, $R_2$ and $R_3$, which may be the same or different, are hydrogen or lower alkyl; and the pharmacologically compatible salts thereof.

By "aryl", there is to be understood a phenyl or naphthyl radical, which can optionally be substituted one or more times. In the case of multiple substitution, the substituents can be the same or different. The lower alkyl or alkoxy substituents of the aryl radical can be straight-chained or branched and contain up to 6 and preferably up to 4 carbon atoms. The halogen atoms can be fluorine, chlorine, bromine or iodine atoms and are preferably fluorine or chlorine. The preferred haloalkyl radical is the trifluoromethyl radical.

Examples of straight-chained or branched, saturated or unsaturated hydrocarbon radicals containing up to 5 carbon atoms, which are represented by B, are alkylene radicals, for example, methylene, methylmethylene, n-butylmethylene, dimethylmethylene, ethylene, 1,1-dimethylethylene, trimethylene and 1,1-dimethyltrimethylene, or alkenylene radicals, for example, vinylene or methylvinylene, with the provise that when A is aryloxy, the carbon atom attached to the oxygen atom has a saturated character.

The lower alkyl radicals $R_1$, $R_2$ and $R_3$ can be straight-chained or branched and can contain up to 6 and preferably up to 3 carbon atoms.

It is to be understood that the above definition of the compounds according to the present invention also includes all possible stereoisomers, as well as mixtures thereof.

The new compounds, as well as their pharmacologically compatible salts, show, in animal experiments, a considerable lowering to the serum lipid level and of the cholesterol level, without undesired side-effect. The new compounds according to the present invention and the salts thereof are, therefore, effective agents against atherosclerosis. Furthermore, they are valuable intermediates for the preparation of antibiotics with a β-lactam structure.

The new compounds of general formula (I) according to the present invention can be prepared by reacting an aminophenol of the general formula:

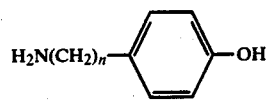

wherein n has the same meaning as above, optionally with intermediate protection of the amino or hydroxyl group, in any desired sequence, with an acid of the general formula:

wherein A and B have the same meanings as above, or with a derivative thereof, and with a compound of the general formula:

wherein $R_1$ and $R_2$ have the same meanings as above, X is a reactive group and Y is the group —$COOR_3$, wherein $R_3$ has the same meaning as above, or Y represents a residue which, after condensation has taken place, is converted into a —$COOR_3$ group, or, when $R_1$ and $R_2$ are lower alkyl radicals, with a mixture of an aliphatic ketone, chloroform and an alkali metal hydroxide, whereafter, if desired, subsequent to the condensation, a particular substituent $R_3$ is converted in known manner into another substituent $R_3$ and the compound obtained is, if desired, converted into a pharmacologically compatible salt.

The process according to the present invention is preferably carried out in two stages. The condensation of the compounds of general formula (II) with derivatives of the carboxylic acids of general formula (III), on the one hand, and with compounds of the general formula (IV), on the other hand, is preferably carried out in such a manner that initially one of the two reactive groups of the compounds (II) is blocked with a protective group which is easily split off, the compound obtained is reacted with a derivative of a carboxylic acid (III) or with a compound (IV), the protective group is again removed and subsequently this reactive intermediate is reacted with the previously unused compound of general formula (IV) or (III).

The reactive derivatives of the carboxylic acids (III) are preferably the halides, anhydrides, mixed carboxylic acid-carbonic acid anhydrides or imidazolides. These can be reacted, for example, under the conditions of a Schotten-Baumann reaction, i.e. with the addition of a tertiary amine, for example, pyridine, dimethylaniline or triethylamine, with a compound (II) in an inert solvent, for example, tetrahydrofuran, dioxan or an excess of the tertiary amine. A previous blocking of the phenolic hydroxyl group by esterification is preferred but etherification with a compound of general formula (IV) is especially preferred. On the other hand, a reactive derivative of a compound (II) can be reacted with a carboxylic acid of general formula (III). Reactive derivatives of compounds (II) include, for example, the phosphorazoamides, which are formed in situ when a phosphorus trihalide, for example phosphorus trichloride, is added to a solution of a compound (II) protected on the hydroxyl group. As solvent and, at the same time as acid acceptor, there can here be used a tertiary amine, for example pyridine. If this reaction is carried out in the presence of a carboxylic acid, then the desired amide with a protected hydroxyl function is obtained directly.

For the reaction of a compound (II) with a compound (IV), it has proved to be advantageous first to convert the amino group of the compound (II) into a protected group, for example a phthalimido group, which, after the reaction, can easily be split off again in known manner, for example, by reaction with hydroxylamine. Other groups known from peptide chemistry can also be used for the protection of the amino group and, after the reaction, split off again. It is preferred to block the amino group with an acyl radical, for example a formyl or acetyl radical, which, after the reaction, can easily be split off again with a strong base, for example sodium hydroxide or potassium hydroxide.

As reactive compounds (IV), those are especially preferred in which X is a radical derived from an anion of a strong acid, for example of a hydrohalic or sulphonic acid. Furthermore, the reaction can be promoted by converting the phenolic hydroxyl group of the compound (II) into a phenolate, for example by reaction with a sodium alcoholate. The reaction of the two components is carried out in a solvent, for example toluene, a xylene, methyl ethyl ketone or dimethyl formamide, preferably with warming.

As substituents Y in compounds of general formula (IV), which can be converted into a —COOR$_3$ group, there can be used, for example, the nitrile, carbaldehyde or hydroxymethyl group.

Instead of a compound (IV), there can also be used a mixture of an appropriate ketone, chloroform and an alkali metal hydroxide; this reaction is preferably carried out with the compound (II) acylated on the amino group, using acetone as the aliphatic ketone (cf. Gazz. Chim. Ital., 77, 431/1947).

The conversion of a substituent R$_3$, which is optionally carried out after the condensation, can be carried out, for example, by saponification of a carboxylic acid ester (R$_3$=alkyl) to give the corresponding carboxylic acid (R$_3$=hydrogen), using a mineral acid or an alkali metal hydroxide in a polar solvent, for example, water, methanol, ethanol, dioxan or acetone. The saponification is advantageously carried out with a strong base, for example sodium or potassium hydroxide, in a mixture of methanol and water at ambient temperature or at a moderately elevated temperature. On the other hand, however, a carboxylic acid can be esterified in the usual manner or an ester with a particular substituent R$_3$ can be converted into an ester with a different R$_3$ substituent by transesterification. Esterification of a carboxylic acid is preferably carried out in the presence of an acidic catalyst, for example hydrochloric acid, sulphuric acid, p-toluene-sulphonic acid or a strongly acidic ion exchange resin. Transesterification, on the other hand, requires the addition of a small amount of a basic substance, for example of an alkali metal or alkaline earth metal hydroxide, or of an alkali metal alcoholate.

For the preparation of salts with pharmacologically compatible organic or inorganic bases, the carboxylic acids are reacted with appropriate bases, for example sodium hydroxide, potassium hydroxide, calcium hydroxide, ammonium hydroxide, methyl-glucamine, morpholine or ethanolamine. Mixtures of carboxylic acids with an appropriate alkali metal carbonate or bicarbonate can also be considered.

For the preparation of pharmaceutical compositions, at least one of the new compounds according to the present invention is mixed with a solid or liquid pharmaceutical diluent or carrier substance and optionally with an aroma, flavoring and/or coloring material and formed, for example, into tablets or dragees or, with the addition of appropriate adjuvants, suspended or dissolved in water or in an oil, for example in olive oil.

The new compounds according to the present invention can be administered orally or parenterally in liquid or solid form. As injection medium, it is preferred to use water which contains the stabilising agents, solubilising agents and/or buffers conventional in the case of injection solutions. Additives of this type include, for example, tartrate and borate buffers, ethanol, dimethyl sulphoxide, complex-forming agents (for example ethylenediaminetetraacetic acid), high molecular weight polymers (for example liquid polyethylene oxide) for viscosity regulation or polyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats or solid high molecular weight polymers (such as polyethylene glycols). Compositions suitable for oral adimnstration can, if desired, contain flavoring and/or sweetening agents. For external use, the compounds (I) according to the present invention can also be used in the form of powders or salves; for this purpose, they are mixed, for example, with powdered, physiologically compatible diluents or conventional salve bases.

The following Examples are given for the purpose of illustrating the present invention:

EXAMPLE 1

2-{4-[2-(4-Chlorocinnamoylamino)-ethyl]-phenoxy}-2-methyl-propionic acid

A mixture of 44.8 g. (0.25 mol) N-acetyl-tyramine, 69.5 g. (0.5 mol) anhydrous powdered potassium carbonate and 750 ml. anhydrous butan-2-one is heated for 2 hours, while stirring at reflux temperature. 73.2 g. (0.375 mol) ethyl α-bromoisobutyrate and 1 g. potassium iodide are then added thereto and the reaction mixture is again heated at reflux temperature.

After 40 hours and again after 70 hours, in each case there are additionally added 35 g. potassium carbonate and 36.6 g. ethyl α-bromoisobutyrate. After a total reaction period of 130 hours, the reaction mixture is evaporated in a vacuum and the residue obtained is poured on to ice water and then extracted with diethyl ether. The ethereal extract is washed three times with 0.5 N aqueous sodium hydroxide solution and then with water, subsequently dried over anhydrous calcium chloride and evaporated. There are obtained 83.8 g. of an oily residue which still contains ethyl α-bromoisobutyrate. The oil is maintained for 5 hours at a vacuum of 0.1 mm.Hg. at 70° C. and then cooled. The resultant crystal slurry is washed with ligroin and dried. There are obtained 69.8 g. (95% of theory) of still not quite pure ethyl 2-[4-(2-acetaminoethyl)-phenoxy]-2-methyl-propionate with a melting point of 48°–51° C.

A solution of 119.1 g. (0.407 mol) ethyl 2-[4-(2-acetaminoethyl)-phenoxy]-2-methylpropionate in 750 ml. ethanol is mixed with a solution of 224.4 g. (4.00 mol) potassium hydroxide in 800 ml. water and heated under reflux for 8 hours. While cooling, there are then added exactly 4.00 mol hydrogen chloride (for example, in the form of 2 N hydrochloric acid), cooling is intensified and, after some time, the crystals which separate out are filtered off with suction. These are washed with water and dried; there are obtained 48.4 g. of product (53% of theory) which melts, with decomposition, at 274° C. From the mother liquor there are obtained, after distilling off the ethanol and cooling, a further 32.5 g. (36% of theory) of product with a melting point of 263°–270° C. The crude 2-[4-(2-aminoethyl)-phenoxy]-2-methylpropionic acid obtained is recrystallised from ethanol and water (4:1 v/v) and then has a melting point of 284° C. The corresponding hydrochloride has a melting point of 187°–189° C.

A solution of 58 g. (0.26 mol) of this carboxylic acid in 600 ml. anhydrous ethanol is gasified, while stirring and cooling with ice, from the surface thereof with dry hydrogen chloride until saturation is reached. The reaction mixture is then left to stand for 12 hours in a closed vessel. Subsequently, the ethanol and hydrogen chloride are removed in a vacuum. Water is added to the residue, followed by extracting three times with diethyl ether. The aqueous phase is then made distinctly alkaline and extracted three times with chloroform. The chloroform extract is washed with a little water, dried over anhydrous potassium carbonate and evaporated. By distillation of the evaporation residue, there are obtained, between 125° and 128° C./0.1 mm.Hg., 53.2 g. (82% of theory) of colorless ethyl 2-[4-(2-aminoethyl)-phenoxy]-2-methylpropionate.

To a solution of 25.1 g. (0.1 mol) ethyl 2-[4-(2-aminoethyl)-phenoxy]-2-methylpropionate in 250 ml. anhydrous pyridine are added, with stirring and in small portions, 20.1 g. (0.1 mol) p-chlorocinnamoyl chloride, the temperature thereby increasing to about 55° C. The reaction mixture is further stirred for 30 minutes and then poured into ice-water, a yellow oil initially separating out. After decanting off the aqueous phase, the oil is triturated with dilute hydrochloric acid and the now solidified mass is taken up in methylene chloride. The solution is washed with water, aqueous sodium bicarbonate solution, dilute hydrochloric acid and again with water, dried over anhydrous calcium chloride and evaporated. After recrystallisation from isopropanol and subsequently from acetone, there are obtained 35.2 g. (84% of theory) ethyl 2-{4-[2-(4-chlorocinnamoylamino)-ethyl]-phenoxy}-2-methylpropionate, which has a melting point of 112°–113° C.

To a solution of 9.15 g. (22 mMol) of this ethyl ester in 50 ml. methanol are added 50 ml. 1 N aqueous potassium hydroxide solution. The reaction mixture is stirred for 2 hours at 45° C., whereafter the methanol is distilled off in a vacuum. After the addition of 10 ml. water, it is extracted with diethyl ether and thereafter mixed with 60 ml. 1 N hydrochloric acid. The precipitate obtained is filtered off with suction, washed with water, dried and recrystallized from acetone. There are obtained 8.0 g. (94% of theory) 2-{4-[2-(4-chlorocinnamoylamino)-ethyl]-phenoxy}-2-methyl-propionic acid; m.p. 164°–165° C.

One of the following two methods can be used for the preparation of the N-acetyl-tyramine used as starting material:

1. 64.0 g. (0.466 mol) tyramine are mixed, while stirring, with 200 ml. acetic anhydride, a clear solution being formed with spontaneous heating up. This solution is seeded with a few crystals of N-acetyl-tyramine, whereafter immediate crystallization takes place. The reaction mixture is cooled rapidly, the crystals are filtered off with suction, washed with diethyl ether and water and dried. There are obtained 59 g. (71% of theory) N-acetyl-tyramine with a melting point of 124°–126° C. By evaporating the mother liquor, dissolving the residue is dilute aqueous sodium hydroxide solution, filtering and acidifying the filtrate, there are obtained a further 5.5 g. (6% of theory) N-acetyl-tyramine with a melting point of 122°–124° C. After recrystallization from ethyl acetate, the N-acetyl-tyramine melts at 129°–131° C.

2. To a solution of 54.9 g. (0.4 mol) tyramine in 200 ml. pyridine are added dropwise, while stirring at 30°–35° C., 65.8 g. (0.84 mol) acetyl chloride. The reaction mixture is subsequently heated for 15 minutes on a boiling waterbath, then cooled and poured into a mixture of ice and water. By the addition of concentrated hydrochloric acid, it is made markedly acidic and subsequently extracted with chloroform. The chloroform phase is washed with water, dried over anhydrous calcium chloride and then evaporated. There is obtained a residue of 88.5 g. (quantitative yield) of diacetyl-tyramine, which melts at 99°–100° C. after recrystallization from benzene. The diacetyl-tyramine is dissolved in 500 ml. methanol. 800 ml. (0.8 mol) 1 N aqueous potassium hydroxide solution are now added thereto, the temperature thereby increasing to about 30° C., and the mixture is subsequently maintained for 2 hours at an internal temperature of 50° C. It is then cooled, weakly acidified with concentrated hydrochloric acid and the methanol evaporated off in a vacuum. The product which crystallizes out is filtered off with suction, thoroughly washed with water and then dried. There are obtained 58.3 g. (81% of theory) N-acetyl tyramine which, after recrystallization from ethyl acetate, has a melting point of 131° C.

The following compounds are prepared in an analogous manner:

(a)

2-{4-[2-(1-Naphthalene-acryloylamino)-ethyl]-phenoxy}-2-methylpropionic acid

From 1-naphthalene-acryloyl chloride and ethyl 2-[4-(2-aminoethyl)-phenoxy]-2-methylpropionate, there is obtained, in 77% yield, ethyl 2-{4-[2-(1-naphthalene-acryloylamino)-ethyl]-phenoxy}-2-methylpropionate which, after recrystallization from diethyl ether, melts at 91°–92° C. and, from this, 2-{4-[2-(1-naphthalene-acryloylamino)-ethyl]-phenoxy}-2-methylpropionic acid in 70% yield which, after recrystallization from ethanol, melts at 184° C.

(b)

2-{4-[2-[3-(4-Chlorophenyl)-propionylamino]-ethyl]-phenoxy}-2-methylpropionic acid From 3-(4-chlorophenyl)-propionyl chloride and ethyl 2-[4-(2-aminoethyl)-phenoxy]-2-methylpropionate, there is obtained, in 90% yield, in the form of a colorless oil, crude ethyl 2-{4-[2-[3-(4-chlorophenyl)-propionylamino]ethyl]-phenoxy}-2-methylpropionate and from this 2-{4-[2-[3-(4-chlorophenyl)-propionylamino]-ethyl]-phenoxy}-2-methylpropionic acid in 64% yield which, after recrystallization from acetone, melts at 110°–111° C.

(c)
2-[4-(4-Chlorophenylacetaminomethyl)-phenoxy]-2-methylpropionic acid

From 4-chlorophenylacetyl chloride and ethyl 2-(4-aminomethylphenoxy)-2-methylpropionate, there is obtained, in 86% yield, in the form of a colorless oil, crude ethyl 2-[4-(4-chlorophenylacetaminomethyl)-phenoxy]-2-methylpropionate and from this 2-[4-(4-chlorophenylacetaminomethyl)-phenoxy]-2-methylpropionic acid in 67% yield which, after recrystallization from acetone, melts at 153°–154° C.

EXAMPLE 2
2-{4-[2-(2-(4-Chlorophenyl)-2-methylpropionylamino)ethyl]-phenoxy}-2-methylpropionic acid.

To a solution of 10.05 g. (40 mMol) ethyl 2-[4-(2-aminoethyl)-phenoxy]-2-methylpropionate in 80 ml. anhydrous pyridine are added dropwise, while stirring at 5°–10° C. in a cooling bath, 9.3 g. (40 mMol) 2-(4-chlorophenyl)-2-methylpropionyl chloride. The cooling bath is removed and, for completion of the reaction, stirring is continued for 30 minutes at ambient temperature. The reaction mixture is then poured on to ice, rendered acidic with concentrated hydrochloric acid and the separated oil is taken up in diethyl ether. The ethereal solution is washed twice with 0.5 N hydrochloric acid and with aqueous sodium bicarbonate solution, dried and evaporated. The residue is recrystallized from 500 ml. ligroin. There are obtained 14.8 g. (86% of theory) ethyl 2-{4-[2-(2-(4-chlorophenyl)-2-methylpropionylamino)-ethyl]-phenoxy}-2-methylpropionate, which melts at 77°–79° C.

14.3 g. (33 mMol) of this ethyl ester are saponified in a mixture of 200 ml. methanol and 50 ml. 1 N aqueous potassium hydroxide solution in a manner analogous to that described in Example 1 and the solid crude product obtained is recrystallized from a mixture of ethyl acetate and ligroin. There are obtained 10.5 g. (78% of theory) 2-{4-[2-(2-(4-chlorophenyl)-2-methylpropionylamino)-ethyl]phenoxy}-2-methylpropionic acid, which melts at 106°–108° C.

The following compounds are obtained in an analogous manner:

(a)
2-{4-[2-(α-Methylcinnamoylamino)-ethyl]-phenoxy}-2-methylpropionic acid

From α-methylcinnamoyl chloride and ethyl 2-[4-(2-aminoethyl)-phenoxy]-2-methylpropionate, there is obtained crude ethyl 2-{4-[2-(α-methylcinnamoylamino)-ethyl]phenoxy}-2-methylpropionate in the form of a colorless oil in a yield of 94% of theory and from this 2-{4-[2-(α-methylcinnamoylamino)-ethyl]-phenoxy}-2-methylpropionic acid in a yield of 62% of theory which, after recrystallization from ethanol, melts at 162°–163° C.

(b)
2-{4-[2-(4-Fluorocinnamoylamino)-ethyl]-phenoxy}-2-methylpropionic acid

From 4-fluorocinnamoyl chloride and ethyl 2-[4-(2-aminoethyl)-phenoxy]-2-methylpropionate, there is obtained ethyl 2-{4-[2-(4-fluorocinnamoylamino)-ethyl]-phenoxy}-2-methylpropionate in a yield of 86% of theory which, after crystallization from ethyl acetate-ligroin, melts at 95°–96° C., and from this 2-{4-[2-(4-fluorocinnamoylamino)ethyl]-phenoxy}-2-methylpropionic acid in a yield of 83% of theory which, after recrystallization from aqueous ethanol, melts at 159°–162° C.

(c)
2-{4-[2-(4-Chlorophenyl)-2-methylpropionylaminomethyl]phenoxy}-2-methylpropionic acid From 2-(4-chlorophenyl)-2-methylpropionyl chloride and ethyl 2-(4-aminomethylphenoxy)-2-methylpropionate, there is obtained crude ethyl 2-{4-[2-(4-chlorophenyl)-2-methylpropionylaminomethyl]-phenoxy}-2-methylpropionate in the form of a colorless oil in a yield of 98% of theory and from this 2-{4-[2-(4-chlorophenyl)-2-methylpropionylaminomethyl]-phenoxy}-2-methylpropionic acid in a yield of 77% of theory which, after recrystallization from ethyl acetate-ligroin, melts at 106°–108° C.

(d)
2-{4-[2-(3-(4-Chlorophenyl)-2,2-dimethylpropionylamino)ethyl]-phenoxy}-2-methylpropionic acid.

From 3-(4-chlorophenyl)-2,2-dimethylpropionyl chloride and ethyl 2-[4-(2-aminoethyl)-phenoxy]-2-methylpropionate, there is obtained crude ethyl 2-{4-[2-(3-(4-chlorophenyl)-2,2-dimethylpropionylamino)-ethyl]-phenoxy}-2-methylpropionate in the form of a colorless oil in a yield of 95% of theory and from this 2-{4-[2-(3-(4-chlorophenyl)-2,2-dimethylpropionylamino)-ethyl]-phenoxy}-2-methylpropionic acid in a yield of 73% of theory which, after recrystallization from ethyl acetate, melts at 132°–134° C.

(e)
2-{4-[2-(2-Methoxycinnamoylamino)-ethyl]-phenoxy}-2-methylpropionic acid From 2-methoxycinnamoyl chloride and ethyl 2-[4-(2-aminoethyl)-phenoxy]-2-methylpropionate, there is obtained crude ethyl 2-{4-[2-(2-methoxycinnamoylamino)-ethyl]phenoxy}-2-methylpropionate in the form of a colorless oil (quantitiative yield) and from this 2-{4-[2-(2-methoxycinnamoylamino)-ethyl]-phenoxy}-2-methylpropionic acid in a yield of 68% of theory which, after recrystallization from ethyl acetate-ligroin, melts at 161°–164° C.

(f)
2-{4-[2-(4-n-Butoxy-3-methoxycinnamoylamino)-ethyl]-phenoxy}-2-methylpropionic acid.

From 4-n-butoxy-3-methoxycinnamoyl chloride and ethyl 2-[4-(2-aminoethyl)-phenoxy]-2-methylpropionate, there is obtained ethyl 2-{4-[2-(4-n-butoxy-3-methoxycinnaomoylamino)ethyl]-phenoxy}-2-methylpropionate in a yield of 90% of theory which, after recrystallization from ethyl acetate-ligroin, melts at 72°–73° C., and from this 2-{4-[2-(4-n-butoxy-3-methoxycinnamoylamino)-ethyl]-phenoxy}-2-methylpropionic acid in a yield of 50% of theory which, after recrystallization from isopropanol, melts at 138.5°–140° C.

(g)
2-{4-[2-(4-Methylcinnamoylamino)-ethyl]-phenoxy}-2-methylpropionic acid.

From 4-methylcinnamoyl chloride and ethyl 2-[4-(2-aminoethyl)-phenoxy]-2-methylpropionate, there is obtained ethyl 2-{4-[2-(4-methylcinnamoylamino)-ethyl]-phenoxy}-2-methylpropionate in a yield of 78% of theory which, after recrystallization from aqueous ethanol, melts at 84°–86.5° C., and from this 2-{4-[2-(4-methyl-cinnamoylamino)ethyl]-phenoxy}-2-methylpropionic acid in a yield of 84% of theory which, after recrystallization from aqueous ethanol, melts at 177°–177.5° C.

EXAMPLE 3

2-{4-[2-(4-Methoxycinnamoylamino)-ethyl]-phenoxy}-2-methylpropionic acid.

A solution of 2.2 g. (55 mMol) sodium hydroxide in 50 ml water is covered with a solution of 12.57 g. (50 mMol) ethyl 2-[4-(2-aminoethyl)-phenoxy]-2-methylpropionate in 75 ml. benzene. While stirring, there are now gradually added 10.81 g. (55 mMol) 4-methoxycinnamoyl chloride. After stirring for 4 hours at ambient temperature, the aqueous phase is separated off, the benzene phase, after filtering, is washed several times with dilute hydrochloric acid, then with an aqueous solution of sodium bicarbonate and with water and thereafter dried over anhydrous calcium chloride. After evaporation in a vacuum, the residue obtained is recrystallized from isopropanol. There are obtained 12.54 g. (61% of theory) colorless ethyl 2-{4-[2-(4-methoxycinnamoylamino)-ethyl]-phenoxy}-2-methylpropionate, which has a melting point of 89°–90° C.

By saponification of this ethyl ester in a manner analogous to that described in Example 1, there is obtained 2-{4-[2-(4-methoxycinnamoylamino)-ethyl]-phenoxy}-2-methylpropionic acid in a yield of 74% of theory which, after recrystallization from ethanol, melts at 158°–159° C.

EXAMPLE 4

2-{4-[2-(2-Chlorocinnamoylamino)-ethyl]-phenoxy}-2-methylpropionic acid

To a mixture of 11.50 g. (63 mMol) o-chlorocinnamic acid, 200 ml. anhydrous tetrahydrofuran and 6.38 g. (63 mMol) anhydrous triethylamine, there are added dropwise at −15° C., 7.50 g. (69 mMol) ethyl chloroformate. The reaction mixture is then stirred for 15 minutes at −15° C. Subsequently, a solution of 15.80 g. (63 mMol) ethyl 2-[4-(2-aminoethyl)phenoxy]-2-methylpropionate in 50 ml. anhydrous tetrahydrofuran is added dropwise thereto and the reaction mixture is stirred for a further 2 hours at −10° C. and then left to stand for a day at ambient temperature. Thereafter, the tetrahydrofuran is distilled off in a vacuum and the residue is taken up in methylene chloride. The methylene chloride phase is extracted with 0.5 N aqueous sodium hydroxide solution, filtered, dried over anhydrous sodium sulphate and evaporated. After recrystallization of the residue from a mixture of ligroin and acetone (30:5 v/v), there is obtained, in a yield of 65% of theory, ethyl 2-{4-[2-(2-chlorocinnamoylamino)-ethyl]-phenoxy}-2-methylpropionate, which melts at 76° C.

By hydrolysis of this ethyl ester in a manner analogous to that described in Example 1, there is obtained 2-{4-[2-(2-chlorocinnamoylamino)-ethyl]-phenoxy}-2-methylpropionic acid in a yield of 80% of theory, which, after recrystallization from isopropanol, melts at 145°–146° C.

EXAMPLE 5

2-{4-[2-(4-Chlorophenyl)-propionylamino)-ethyl]-phenoxy}-2-methylpropionic acid.

A mixture of 9.23 g. (50 mMol) 2-(4-chlorophenyl)-propionic acid, 12.6 g. (50 mMol) ethyl 2-[4-(2-aminoethyl)phenoxy]-2-methylpropionate and 100 ml. dry pyridine is mixed at 0°–5° C., while stirring, with 2.2 ml. (25 mMol) phosphorus trichloride and left to stand for 3 days at 5°–10° C. The reaction mixture is then poured on to ice, acidified with 2 N hydrochloric acid and the oil which separates is taken up in diethyl ether. The ethereal solution is washed twice with 0.5 N hydrochloric acid and with aqueous sodium bicarbonate solution, then dried and evaporated. As residue, there are obtained 17.1 g. (82% of theory) crude ethyl 2-{4-[2-(4-chlorophenyl)-propionylaminoethyl]-phenoxy}-2-methylpropionate in the form of a bright yellow oil.

A solution of 15.8 g. (38 mMol) of this ethyl ester in a mixture of 200 ml. methanol and 57 ml. 1 N aqueous potassium hydroxide solution is warmed to 45° C. for 2 hours and then evaporated to dryness in a vacuum. The residue is taken up in water, washed twice with diethyl ether and the aqueous phase then acidified. The oil which separates is taken up in diethyl ether or in methylene chloride and the solution obtained is dried over anhydrous sodium sulphate and the solvent is distilled off. Since the product is obtained in the form of an oil, purification thereof is carried out by dissolving it in a stoichiometric amount of 1 N aqueous sodium hydroxide solution and evaporating the solution obtained to give the corresponding sodium salt. (In the following Example, such a purification is not necessary). There are obtained 10.8 g. (69% of theory) sodium 2-{4-[2-(2-(4-chlorophenyl)-propionylamino)-ethyl]phenoxy}-2-methylpropionate. This sodium salt melts in the range of from 150° to 155° C.

The following compound is prepared in an analogous manner:

2-{4-[2-(4-Chlorophenylacetamino)-ethyl]-phenoxy}-2-methylpropionic acid.

From 4-chlorophenylacetic acid and ethyl 2-[4-(2-aminoethyl)-phenoxy]-2-methylpropionate there is obtained crude ethyl 2-{4-[2-(4-chlorophenylacetamino)-ethyl]phenoxy}-2-methylpropionate in the form of a colorless oil in a yield of 56% of theory and from this 2-{4-[2-(4-chlorophenylacetamino)-ethyl]-phenoxy}-2-methylpropionic acid in a yield of 60% of theory which, after recrystallization from ethyl acetate, melts at 115° C.

EXAMPLE 6

2-{4-[3-(4-Chlorocinnamoylamino)-propyl]-phenoxy}-2-methylpropionic acid

A solution of 7.6 g. (48 mMol) 4-(3-aminopropyl)-phenol in 100 ml. anhydrous pyridine is mixed with 20.0 g. (96 mMol) 4-chlorocinnamoyl chloride. The reaction mixture is heated for 15 minutes, with stirring, at 80°–90° C., then cooled somewhat and poured into 2 liters ice-water. The precipitate obtained is filtered off with suction and dried. There is obtained, in quantitative yield, the 4-[3-(4-chlorocinnamoylamino)-propyl]-phenyl ester of 4-chlorocinnamic acid which, after recrystallization from ethyl ester-ligroin, melts at 159°–161.5° C.

A mixture of 22.9 g. (47 mMol) of this ester, 250 ml. methanol and 75 ml. (milliequivalents) 1 N aqueous potassium hydroxide solution is stirred for 6 hours at 40°–50° C. Subsequently, the reaction mixture is mixed with 75 ml. (75 milliequivalents) 1 N hydrochloric acid. The precipitate obtained is filtered off with suction and the resultant 4-chlorocinnamic acid washed out with aqueous sodium bicarbonate solution. After further washing with water, suction filtration and drying, the product obtained is recrystallized from a mixture of ethyl acetate and ligroin. There are obtained 14.2 g. (96% of theory) 4-[3-(4-chlorocinnamoylamino)-propyl]-phenol, which melts at 127°–129° C.

A mixture of 15.1 g. (48 mMol) of this substituted phenol, 13.2 g. (96 mMol) anhydrous potassium carbonate and 250 ml. butan-2-one is heated for 2 hours, while stirring at reflux temperature. There are then added thereto 14.1 g. (72 mMol) ethyl 2-bromo-2-methylpropionate, as well as a spatula tip of potassium iodide and the mixture is kept under reflux for 24 hours. After a further addition of 7.0 g. (36 mMol) ethyl 2-bromo-2-methylpropionate and of 6.6 g. (48 mMol) potassium carbonate, heating under reflux is continued for a further 48 hours.

The reaction mixture is subsequently filtered with suction, the filtrate is evaporated and the residue is taken up in chloroform. The chloroform phase is extracted with 2 N aqueous sodium hydroxide solution, washed neutral dried over anhydrous calcium chloride and the chloroform subsequently evaporated off. The evaporation residue is recrystallized from a mixture of ethyl acetate and ligroin. There are obtained 14.2 g. (69% of theory) ethyl 2-{4-[3-(4-chlorocinnamoylamino)-propyl]-phenoxy}-2-methylpropionate, which melts at 85°–88° C.

To a solution of 14.0 g. (32.6 mMol) of this ethyl ester in 150 ml. methanol, there are added 50 ml. (50 milliequivalents) 1 N aqueous potassium hydroxide solution. The reaction mixture is stirred for 2 hours at 45° C. and then 50 ml. (50 milliequivalents) 1 N hydrochloric acid added thereto dropwise. The methanol is distilled off and the fine crystalline precipitate obtained is filtered off with suction. This is washed with water, dried and recrystallized from a mixture of ethyl acetate and ligroin. There are obtained 9.6 g. (73% of theory) 2-{4-[3-(4-chlorocinnamoylamino)-propyl]-phenoxy}-2-methylpropionic acid, which melts at 143°–145° C.

EXAMPLE 7

2-{4-[2-(4-Chlorophenoxyacetamino)-ethyl]-phenoxy}-2-methylpropionic acid

To a solution of 18.0 g. (72 mMol) ethyl 2-[4-(2-aminoethyl)-phenoxy]-2-methylpropionate in 36 ml. anhydrous pyridine in a cooling bath, there are added dropwise at 5°–10° C., while stirring, 14.7 g. (72 mMol) 4-chlorophenoxyacetyl chloride. The cooling bath is removed and, for completion of the reaction, stirring is continued for 30 minutes at ambient temperature. The reaction mixture is then poured on to ice, acidified with concentrated hydrochloric acid and the oil which separates out is taken up in chloroform. The chloroform solution is washed twice with 0.5N hydrochloric acid and with aqueous sodium bicarbonate solution, dried and evaporated. Since the product is obtained in the form of an oil, it is, in this case, purified by chromatographing on silica gel with a mixture of toluene and chloroform. (In the following Examples, such as purification is not necessary). There are obtained 25.0 g. (83% of theory) ethyl 2-{4-[2-(4-chlorophenoxyacetamino)-ethyl]-phenoxy}-2-methylpropionate which, after recrystallization from ligroin-ethyl acetate, melts at 61°–63° C.

12.0 g. (28.6 mMol) of the ethyl ester thus obtained are saponified in a mixture of 57 ml. methanol and 57 ml. 1N aqueous potassium hydroxide solution in a manner analogous to that described in Example 1 and the crude solid product obtained is recrystallized from a mixture of ethyl acetate and ligroin. There are obtained 7.0 g. (61% of theory) 2-{4-[2-(4-chlorophenoxyacetamino)-ethyl]phenoxy}-2-methylpropionic acid, which melts at 139°–141° C.

The following compounds are prepared in an analogous manner:

(a)

2-{4-[2-(2-(4-Chlorophenoxy)-2-methylporpionylamino)ethyl]-phenoxy}-2-methylpropionic acid.

From 2-(4-chlorophenoxy)-2-methylpropionyl chloride and ethyl 2-[4-(2-aminoethyl)-phenoxy]-2-methylpropionate, there is obtained ethyl 2-{4-[2-(2-(4-chlorophenoxy)-2-methylpropionylamino)-ethyl]-phenoxy}-2-methylpropionate in a yield of 60% of theory which, after recrystallization from ligroin, melts at 65°–67° C. and from this 2-{4-[2(2-(4-chlorophenoxy)-2-methylpropionylamino)-ethyl]-phenoxy}2-methylpropionic acid in a yield of 69% of theory which, after recrystallization from ligroin-ethyl acetate, melts at 109°–112° C.

(b)

2-{4-[2-(2-(4-Chlorophenoxy)-propionylamino)-ethyl]-phenoxy}-2-methylpropionic acid.

From 2-(4-chlorophenoxy)-propionyl chloride and ethyl 2-[4-(2-aminoethyl)-phenoxy]-2-methylpropionate, there is obtained ethyl 2-{4-[2-(2-(4-chlorophenoxy)-propionylamino)ethyl]-phenoxy}-2-methylpropionate in a yield of 87% of theory which, after recrystallization from isopropanol-ligroin, melts at 78.5°–79° C. and from this 2-{4-[2-(2-(4-chlorophenoxy)-propionylamino)-ethyl]-phenoxy}-2-methylpropionic acid in a yield of 85% of theory, the sodium salt which which, after recrystallization from isopropanol, melts at 200°–201° C.

(c)

2-{4-[2-(2-(4-Fluorophenoxy)-2-methylpropionylamino)ethyl]-phenoxy}-2-methylpropionic acid From 2-(4-fluorophenoxy)-2-methylpropionyl chloride and ethyl 2-[4-(2-aminoethyl)-phenoxy]-2-methylpropionate, there is obtained ethyl 2-{4-[2-(2-(4-fluorophenoxy)-2-methylpropionylamino)-ethyl]-phenoxy}-2-methylpropionate in a yield of 77% of theory which, after recrystallization from diethyl ether, melts at 91°–92° C. and from this 2-{4-[2-(2-(4-fluorophenoxy)-2-methylpropionylamino)ethyl]-phenoxy}-2-methylpropionic acid in a yield of 51% of theory which, after-recrystallization from ethyl acetate-ligroin, melts at 113°–114° C.

(d)

2-{4-[2-(2-(3-Methylphenoxy)-2-methylpropionylamino)ethyl]-phenoxy}-2-methylpropionic acid.

From 2-(3-methylphenoxy)-2-methylpropionyl chloride and ethyl 2-[4-(2-aminoethyl)-phenoxy]-2-methylpropionate, there is obtained crude ethyl 2-{4-[2-(2-(3-methylphenoxy)2-methylpropionylamino)-ethyl]-phenoxy}-2-methylpropionate in the form of a colorless oil, in quantitative yield, from which is obtained 2-{4-[2-(2-(3-methylphenoxy)-2-methylpropionylamino)-ethyl]-phenoxy}-2-methylpropionic acid in a yield of 90% of theory which, after recrystallization from ethyl acetate-ligroin, melts at 85°–88° C.

EXAMPLE 8

[4-(4-Chloro-2,6-dimethylphenoxyacetaminomethyl)-phenoxy]acetic acid 80.0 g. (344 mMol) 4-chloro-2,6-dimethylphenoxyacetyl chloride are added, while stirring, to a mixture of 27.1 g. (170 mMol) 4-hydroxybenzylamine hydrochloride, 23.5 g. (170 mMol) pulverized potassium carbonate and 400 ml. anhydrous pyridine. The reaction mixture is heated on a boiling waterbath for 15 minutes and then cooled to about 30° C. The flask contents are poured on to ice and, after standing overnight, are filtered with suction. The filter cake is digested with an aqueous solution of sodium bicarbonate, washed with water and dried. After recrystallization from acetone, there are obtained 75.5 g. (86% of theory) of the [4-(4-chloro-2,6-dimethylphenoxyacetaminomethyl)-phenyl ester] of 4-chloro-2,6-dimethylphenoxyacetic acid, which melts at 158° C.

To a suspension of 63.0 g. (122 mMol) of this ester in 200 ml. methanol, there are added 300 ml. 1 N aqueous potassium hydroxide solution. The reaction mixture is stirred for 1 hour at 40°-50° C., left to stand overnight and then 320 ml. 1 N hydrochloric acid are slowly added thereto dropwise. The precipitate obtained is filtered off with suction and stirred with an aqueous solution of sodium bicarbonate. After filtering off with suction, washing with water and drying, the product is recrystallized from ethanol. There are obtained 35.2 g. (90% of theory) 4-(4-chloro-2,6-dimethylphenoxyacetaminomethyl)-phenol, which melts at 144° C.

A mixture of 14.3 g. (44.7 mMol) of this substituted phenol, 6.9 g. (50 mMol) pulverized potassium carbonate and 250 ml. anhydrous butan-2-one is maintained for 2 hours at reflux temperature, then cooled and 1 g. potassium iodide and 11.7 g. (70 mMol) ethyl bromoacetate added thereto. The reaction mixture is now kept at reflux temperature for 8 hours, thereafter filtered with suction and the filtrate evaporated in a vacuum. The oily evaporation residue is taken up in chloroform. The chloroform solution is extracted several times with 0.5 N aqueous sodium hydroxide solution, washed neutral with water, dried over anhydrous calcium chloride and evaporated. After recrystallization of the evaporation residue from ethanol, there are obtained 12.2 g. (67% of theory) ethyl [4-(4-chloro-2,6-dimethylphenoxyacetaminomethyl)-phenoxy]-acetate, which melts at 88° C.

6.7 g. (16.5 mMol) ethyl [4-(4-chloro-2,6-dimethylphenoxyacetaminomethyl)-phenoxy]-acetate are suspended in 70 ml. methanol. After the addition of 36 ml. 1 N aqueous potassium hydroxide solution, the reaction mixture is stirred for 2 hours at 40°-50° C., cooled and 40 ml. 1 N aqueous potassium hydroxide solution added thereto. The product which precipitates out is filtered off with suction, washed with water and dried. After recrystallization from acetone, there are obtained 6.0 g. (96% of theory) [4-(4-chloro-2,6-dimethylphenoxyacetaminomethyl)-phenoxy]-acetic acid, which melts at 166°-167° C.

The following compound is prepared in an analogous manner:

4-[2-(4-Chloro-2,6-dimethylphenoxyacetamino)-ethyl]phenoxyacetic acid by hydrolysis of the corresponding ethyl ester, the yield being 60% of theory and the compound melting, after recrystallization from acetone, at 154°-155° C. The ethyl ester is obtained via the following intermediates: N.O,bis-(4-chloro-2,6-dimethylphenoxyacetyl)-tyramine (from tyramine and 2 mol 4-chloro-2,6-dimethylphenoxyacetyl chloride); yield 76% of theory, m.p. 145°-146° C., after recrystallization from acetone; N-(4-chloro-2,6-dimethylphenoxyacetyl)-tyramine (by partial hydrolysis of the bis compound); yield 81% of theory; m.p. 118°-119° C., after recrystallization from ethanol; ethyl 4-[2-(4-chloro-2,6-dimethylphenoxyacetamino)-ethyl]phenoxyacetate (from N-(4-chloro-2,6-dimethylphenoxyacetyl)tyramine and ethyl bromoacetate); yield 74% of theory; m.p. 104°-105° C., after recrystallization from ethanol.

EXAMPLE 9

2-[4-(4-Chloro-2,6-dimethylphenoxyacetaminomethyl)-phenoxy]-2-methylpropionic acid A mixture of 11.0 g. (34.4 mMol) 4-(4-chloro-2,6-dimethylphenoxyacetaminomethyl)-phenol, 4.8 g. (35 mMol) pulverized potassium carbonate and 100 ml. anhydrous butan-2-one is maintained for 2 hours at reflux temperature, then cooled and 0.5 g. potassium iodide and 13.45 g. (69 mMol) ethyl 2-bromo-2-methylpropionate added thereto. The reaction mixture is then stirred for 15 hours at 80° C. and thereafter filtered with suction. The filtrate is evaporated in a vacuum, the residue is taken up in diethyl ether and the ethereal phase is extracted several times with 0.5 N aqueous sodium hydroxide solution. Subsequently, it is washed neutral, dried over anhydrous calcium chloride and evaporated. After recrystallization of the residue from ethyl acetate, there are obtained 10.8 g. (73% of theory) ethyl 2-[4-(4-chloro-2,6-dimethylphenoxyacetaminomethyl)-phenoxy]-2-methylpropionate, which melts at 99°-100° C.

A mixture of 7.8 g. (18 mMol) ethyl 2-[4-(4-chloro-2,6-dimethylphenoxyacetaminomethyl)-phenoxy]-2-methylpropionate, 40 ml. methanol and 40 ml. 1 N aqueous potassium hydroxide solution is stirred for 1 hour at 40° C., then cooled and 42 ml. 1 N hydrochloric acid added thereto dropwise, the free acid thereby precipitating out. This is filtered off with suction, washed with water, dried and recrystallized from a mixture of isopropanol and ligroin. There are obtained 4.2 g. (58% of theory) 2-[4-(4-chloro-2,6-dimethylphenoxyacetaminomethyl)-phenoxy]-2-methylpropionic acid with a melting point of 112°-113° C.

The following compound is obtained in an analogous manner:

2-{4-[2-(4-chloro-2,6-dimethylphenoxyacetamino)-ethyl]phenoxy}-2-methylpropionic acid by hydrolysis of the corresponding ethyl ester; it is obtained in a yield of 57% of theory and, after recrystallization from acetone, melts at 185°-186° C.

The ethyl 2-{4-[2-(4-chloro-2,6-dimethylphenoxyacetamino)-ethyl]-phenoxy}-2-methylpropionate is obtained from N-(4-chloro-2,6-dimethylphenoxyacetyl)-tyramine and ethyl 2-bromo-2-methylpropionate in a yield of 86% of theory; after recrystallization from ligroin, it melts at 70°-71° C.

EXAMPLE 10

2-{4-[2-(4-Chloro-2,6-dimethylphenoxyacetamino)-ethyl]phenoxy}-2-methylpropionic acid To a suspension of 20.0 g. (0.06 mol) N-(4-chloro-2,6-dimethylphenoxyacetyl)-tyramine in 285 ml. anhydrous acetone, there are added 28.6 g. (0.51 mol) pulverized potassium hydroxide. Subsequently, 32.3 g. (0.27 mol)

chloroform are added dropwise so slowly that the flask content boils gently. The reaction mixture is thereafter stirred for 2 hours at boiling temperature and the reaction mixture is then poured into water. The aqueous solution is washed with chloroform and finally the desired acid is precipitated out by acidification with hydrochloric acid. After recrystallization from acetone, there are obtained 15.9 g. (63% of theory) 2-{4-[2-(4-chloro-2,6-dimethylphenoxyacetamino)-ethyl]-phenoxy}-2-methylpropionic acid, which melts at 183°–184° C. All the physical constants of the product are identical with those of the product obtained according to Example 9.

EXAMPLE 11

The following compounds are obtained in a manner analogous to that described in Example 1:

(a)

2-{4-[2-(3,4-Dichlorocinnamoylamino)-ethyl]-phenoxy}-2-methylpropionic acid.

From 3,4-dichlorocinnamoyl chloride and ethyl 2-[4-(2-aminoethyl)-phenoxy]-2-methylpropionate, there is obtained, in a yield of 70% of theory, ethyl 2-{4-[2-(3,4-dichlorocinnamoylamino)-ethyl]-phenoxy}-2-methylpropionate which, after recrystallization from ethanol, melts at 107°–108° C. and from this 2-{4-[2-(3,4-dichlorocinnamoylamino)ethyl]-phenoxy}-2-methylpropionic acid in a yield of 84% of theory which, after recrystallisation from isopropanol, melts at 170°–171° C.

(b)

2-{4-[2-(2,5-Dimethylcinnamoylamino)-ethyl]-phenoxy}-2-methylpropionic acid

From 2,5-dimethylcinnamoyl chloride and ethyl 2-[4-(2-aminoethyl)-phenoxy]-2-methylpropionate, there is obtained, in a yield of 72% of theory, ethyl 2-{4-[2-(2,5-dimethylcinnamoylamino)-ethyl]-phenoxy}-2-methylpropionate which, after recrystallization from ligroin, melts at 80°–81° C. and from this 2-{4-[2-(2,5-dimethylcinnamoylamino)-ethyl]-phenoxy}-2-methylpropionic acid in a yield of 86% of theory which, after recrystallization from isopropanol, melts at 172°–173° C.

(c)

2-{4-[2-(3-Trifluoromethylcinnamoylamino)-ethyl]-phenoxy}-2-methylpropionic acid From 3-trifluoromethylcinnamoyl chloride and ethyl 2-[4-(2-aminoethyl)-phenoxy]-2-methylpropionate, there is obtained, in a yield of 97% of theory, crude ethyl 2-{4-[2-(3-trifluoromethylcinnamoylamino)-ethyl]-phenoxy}-2-methylpropionate in the form of a colorless oil and from this 2-{4-[2-(3-trifluoromethylcinnamoylamino)-ethyl]-phenoxy}-2-methylpropionic acid in a yield of 76% of theory which, after recrystallization from ethyl acetate and ligroin, melts at 147°–149° C.

(d)

2-{{4-{2-[4-(4-Chlorophenyl)-2,2-dimethylbutyroylamino]-ethyl}-phenoxy}}-2-methylpropionic acid.

From 4-(4-chlorophenyl)-2,2-dimethylbutyroyl chloride and ethyl 2-[4-(2-aminoethyl)-phenoxy]-2-methylpropionate, there is obtained, in a yield of 96% of theory, crude ethyl 2-{{4-{2-[4-(4-chlorophenyl)-2,2-dimethylbutyroylamino]ethyl}-phenoxy}}-2-methylpropionate in the form of a colorless oil and from this 2-{{4-{2-[4-(4-chlorophenyl)2,2-dimethylbutyroylamino]-ethyl}-phenoxy}}-2-methylpropionic acid in a yield of 81% of theory which, after recrystallization from diethyl ether, melts at 113°–114° C.

(e)

2-{{4-{2-[4-(4-Chlorophenyl)-butyroylamino]-ethyl}-phenoxy}}-2-methylpropionic acid From 4-(4-chlorophenyl)-butyroyl chloride and ethyl 2-[4-(2-aminoethyl)-phenoxy]-2-methylpropionate, there is obtained, in a yield of 82% of theory, crude ethyl 2-{{4-{2-[4-(4-chlorophenyl)-butyroylamino]-ethyl}-phenoxy}}2-methylpropionate in the form of a colorless oil and from this 2-{{2-{2-[4-(4-chlorophenyl)-butyroylamino]-ethyl}phenoxy}}-2-methylpropionic acid in the form of its potassium salt in a yield of 90% of theory, which has a melting point of 135°–138° C.

(f)

2-{4-[2-(2-(4-Chlorophenoxy)-hexanoylamino)-ethyl]-phenoxy}-2-methylpropionate.

From 2-(4-chlorophenoxy)-hexanoyl chloride and ethyl 2-[4-(2-aminoethyl)-phenoxy]-2-methylpropionate, there is obtained, in a yield of 92% of theory, pure ethyl 2-{4-[2-(2-(4-chlorophenoxy)-hexanoylamino)-ethyl]-phenoxy}-2-methoxypropionate ($n_D^{20}=1.5310$) and from this 2-{4-[2-(2-(4-chlorophenoxy)-hexanoylamino)-ethyl]-phenoxy}-2-methylpropionate.

(g) 2-{{4-{2-[2-(3-Trifluoromethylphenoxy)-2-methylpropionylamino]-ethyl}-phenoxy}}-2-methylpropionic acid From 2-(3-trifluoromethylphenoxy)-2-methyl-propionyl chloride and ethyl 2-[4-(2-aminoethyl)-phenoxy]-2-methylpropionate, there is obtained, in a yield of 89% of theory, crude ethyl 2-{{4-{2-[2-(3-trifluoromethylphenoxy)-2-methylpropionylamino]-ethyl}-phenoxy}}-2-methylpropionate in the form of a colorless oil and from this 2-{{4-{2-[2-(3-trifluoromethylphenoxy)-2-methylpropionylamino]-ethyl}-phenoxy}}-2-methylpropionic acid in a yield of 80% of theory which, after recrystallization from ligroin and isopropanol (9:1 v/v), melts at 101°–102° C.

EXAMPLE 12

2-{{4-{2-[2-(3-Methoxyphenoxy)-2-methylpropionylamino]-ethyl}-phenoxy}}-2-methylpropionic acid In a manner analogous to that described in Example 4, from 2-(3-methoxyphenoxy)-2-methylpropionic acid and ethyl 2-[4-(2-aminoethyl)-phenoxy]-2-methylpropionate, in the presence of triethylamine and ethyl chloroformate, there is obtained, in a yield of 84% of theory, ethyl 2-{{4-{2-[2-(3-methoxyphenoxy)-2-methylpropionylamino]-ethyl}-phenoxy}}-2-methylpropionate which, after recrystallization from cyclohexane and ethyl acetate, melts at 68°–69° C. and from this 2-{{4-{2-[2-(3-methoxyphenoxy)-2-methylpropionylamino]-ethyl}-phenoxy}}-2-methylpropionic acid in a yield of 64% of theory which, after recrystallization from cyclohexane and ethyl acetate, melts at 80°–81° C.

The ability of the instant compounds to lower the serum lipid level and the cholesterol level is demonstrated by the following illustrative experiments:

Healthy male Sprague-Dawley rats of a weight of about 200 g were given either (a) a powdered fodder of the company Intermast, Bockhum-Hövel (manufacturer: Plange Soest) which contained admixed thereto the test compounds (in the concentrations listed below) or (b) doses of the test compounds suspended in methylcellulose administered by way of a stomach tube (the dosage in mg/kg is indicated below).

This treatment continued uniformly for seven days. Two hours after the last administration the animals were killed by neck blow and bled white. The triglycerides in the serum were then determined enzymatically according to Kreutz and Eggstein (Klin. Wschr. 40, 363, 1962; 44, 262/1966) in the modification according to Schmidt et al (Zeitschrift für klin. Chem. und Klin. Biochem. 6, 156/1968) and cholesterol was determined colorimetrically according to Watson (Clin. Chim. Acta 5, 637, 1960).

The control animals were given perorally carrier substances or the laboratory diet without the test compound. The results, expressed as percent-reduction as compared to the control animals, are set out in the following Table:

administered in the course of a day, i.e., about four applications of 500 mg. each at spaced time intervals or 8 of about 250 mg. each. A convenient form of administration is in a gelatin capsule.

For the preparation of pharmaceutical compositions, at least one of the new compounds (I) is mixed with a solid or liquid pharmaceutical carrier or diluent and optionally with an odoriferous, flavoring and/or coloring material and formed, for example, into tablets or dragees, or with the addition of appropriate adjuvants, suspended or dissolved in water or in an oil, for example, olive oil.

The compounds (I) can be administered orally or parenterally in liquid or solid form. As injection medium, it is preferred to use water which contains the stabilizing agents, solubilizing agents and/or buffers, conventional for injection solutions. Additives of this type include, for example, tartrate and borate buffers, ethanol, dimethyl sulphoxide, complex-forming agents

TABLE

| Test Compound | Prep. Example No. | Concentration in the Fodder in % | Reduction in % Triglycerides | Reduction in % Cholesterol |
|---|---|---|---|---|
| 2-(p-chlorophenoxy)-2-methyl-propionic acid ethyl ester (= Clofibrat) Comparison Compound | | 0.056 | 21 | 0 |
| 2-{4-[2-(4-chlorophenoxyacet-amino)-ethyl]-phenoxy}-2-methyl-propionic acid | 7 | 0.025 | 51 | 15 |
| 2-{4-[2-(4-chlorophenylacet-amino)-ethyl]-phenoxy}-2-methyl-propionic acid | 5(a) | 0.025 | 51 | 14 |
| 2-{4-[2-($\alpha$-methylcinnamoylamino)-ethyl]-phenoxy}-2-methylpropionic acid | 2(a) | 0.050 | 65 | 22 |
| 2-{4-[2-(4-fluorocinnamoylamino)-ethyl]-phenoxy}-2-methylpropionic acid | 2(b) | 0.050 | 74 | 35 |
| 2-{4-[3-(4-chlorocinnamoyl-amino)-propyl]-phenoxy}-2-methylpropionic acid | 6 | 0.050 | 78 | 21 |
| 2-{4-[2-(2-methoxycinnamoyl-amino)-ethyl]-phenoxy}-2-methyl-propionic acid | 2(e) | 0.050 | 78 | 4 |
| 2-{4-[2-(4-chlorocinnamoyl-amino)-ethyl]-phenoxy}-2-methyl-propionic acid | 1 | 0.005 | 45 | 16 |
| 2-{4-[2-(3,4-dichlorocinnamoyl-amino)-ethyl]-phenoxy}-2-methyl-propionic acid | 11(a) | 0.025 | 60 | 20 |
| | | Dosage in mg/kg (suspended in methyl-cellulose) | | |
| 2-{4-[2-(2-chlorophenoxy)-2-methylpropionylamino)-ethyl]-phenoxy}-2-methylpropionic acid | 7(a) | 50 | 67 | 32 |
| 2-{4-[2-(2-chlorocinnamoylamino)-ethyl]-phenoxy}-2-methylpropionic acid | 4 | 25 | 51 | 11 |
| 2-{{4-{2-[4-(4-chlorophenyl)-2,2-dimethylbutyroylamino]-ethyl}-phenoxy}}-2-methylpropionic acid | 11(d) | 12.5 | 54 | 4 |

From the above it can be seen that the new substances are superior to the known anti-hyperlipidaemic, Clofibrat, in particular with respect to cholesterol-reducing action.

The novel compounds may be administered by themselves or in conjunction with carriers which are pharmacologically acceptable, either active or inert. The dosage units are similar to those of the heretofore known anti-cholesterol agents, e.g., about 1 to 2 grams per day for an adult or about 30 mg/kg per day although higher or lower dosages can be used. Rather than a single dose it is preferable if the compounds are (such as ethylene diaminetetraacetic acid), high molecular weight polymers (such as liquid polyethylene oxide) for viscosity regulation or polyoxyethylene derivatives of sorbitan anhydrides.

Solid carrier materials include, for example, starch, lactose, mannitol, methyl cellulose, talc, highly dispersed silicic acid, high molecular weight fatty acids (such as stearic acid), gelatine, agar-agar, calcium phosphate, magnesium stearate, animal and vegetable fats and solid high molecular weight polymers (such as polyethylene glycols). Compositions suitable for oral administration can, if desired, contain flavoring and sweetening agents. For topical application, the compounds (I) according to the present invention can also be employed in the form of powders and salves. For this purpose, they are mixed with, for example, powdered, physiologically compatible diluents or with conventional salve bases.

It will be appreciated that the instant specification and examples are set forth by way of illustration and not limitation, and that various modifications and changes may be made without departing from the spirit and scope of the present invention.

What is claimed is:

1. Phenoxyalkylcarboxylic acid compound of the formula

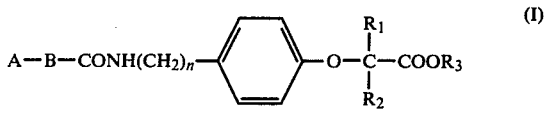

wherein
A is aryl, aryloxy, substituted aryl or substituted aryloxy, wherein said aryl is selected from phenyl and naphthyl and wherein the substituents are selected from lower alkyl, lower alkoxy, halogen and haloalkyl;
B is a straight-chained or branched, saturated or unsaturated hydrocarbyl containing up to 5 carbon atoms;
n is 1, 2 or 3 and
$R_1$, $R_2$ and $R_3$, which may be the same or different, are hydrogen or lower alkyl; and the pharmacologically compatible salts thereof.

2. Phenoxyalkylcarboxylic acid compound as claimed in claim 1, wherein A is phenyl.

3. Phenoxyalkylcarboxylic acid compound as claimed in claim 1, wherein A is phenoxy.

4. Phenoxyalkylcarboxylic acid compound as claimed in claim 1, wherein A is alkylaryl.

5. Phenoxyalkylcarboxylic acid compound as claimed in claim 1, wherein A is alkylaryloxy.

6. Phenoxyalkylcarboxylic acid compound as claimed in claim 1, wherein A is alkoxyaryl.

7. Phenoxyalkylcarboxylic acid compound as claimed in claim 1, wherein A is alkoxyaryloxy.

8. Phenoxyalkylcarboxylic acid compound as claimed in claim 1, wherein A is halophenyl.

9. Phenoxyalkylcarboxylic acid compound as claimed in claim 1, wherein A is halophenoxy.

10. Phenoxyalkylcarboxylic acid compound as claimed in claim 1, wherein A is haloalkylphenyl.

11. Phenoxyalkylcarboxylic acid compound as claimed in claim 1, wherein A is haloalkylphenoxy.

12. Phenoxyalkylcarboxylic acid compound as claimed in claim 1, wherein B is alkylene of up to 5 carbon atoms.

13. Phenoxyalkylcarboxylic acid compound as claimed in claim 1, wherein B is alkenylene of up to 5 carbon atoms.

14. Phenoxyalkylcarboxylic acid compound as claimed in claim 1, wherein A is phenoxy and B is alkylene of up to 5 carbon atoms.

15. Phenoxyalkylcarboxylic acid compound as claimed in claim 1, wherein n is 1.

16. Phenoxyalkylcarboxylic acid compound as claimed in claim 1, wherein n is 2.

17. Phenoxyalkylcarboxylic acid compound as claimed in claim 1, wherein n is 3.

18. Phenoxyalkylcarboxylic acid compound as claimed in claim 1, wherein at least one of $R_1$, $R_2$ and $R_3$ is hydrogen.

19. Phenoxyalkylcarboxylic acid compound as claimed in claim 1, wherein at least one of $R_1$, $R_2$ and $R_3$ is lower alkyl.

20. Phenoxyalkylcarboxylic acid compound as claimed in claim 1 designated 2-{4-[2-(4-chlorocinnamoylamino)-ethyl]phenoxy}-2-methylpropionic acid.

21. Phenoxyalkylcarboxylic acid compound as claimed in claim 1 designated 2-{4-[2-(4-fluorocinnamoylamino)-ethyl]phenoxy}-2-methylpropionic acid.

22. Phenoxyalkylcarboxylic acid compound as claimed in claim 1 designated 2-{4-[3-(4-chlorocinnamoylamino)-propyl]-phenoxy}-2-methylpropionic acid.

23. Phenoxyalkylcarboxylic acid compound as claimed in claim 1 designated 2-{4-[2-(3,4-dichlorocinnamoylamino)-ethyl]phenoxy}-2-methylpropionic acid.

24. Phenoxyalkylcarboxylic acid compound as claimed in claim 1 designated 2-{{4-{2-[4-(4-chlorophenyl)2,2-dimethylbutyroylamino]-ethyl}-phenoxy}}-2-methylpropionic acid.

25. Therapeutic compositions for depressing triglycerides and serum-lipids in mammals comprising a pharmacologically acceptable carrier and, in therapeutically effective amounts, a phenoxyalkylcarboxylic acid compound as claimed in claim 1.

26. Method of depressing the serum-lipid and triglyceride content in mammals, which method comprises administering thereto an effective amount of a phenoxyalkylcarboxylic acid compound as claimed in claim 1.

27. Method as claimed in claim 26, wherein said compound is applied at a dosage of about 30 mg/kg per day.

28. Method as claimed in claim 26, wherein said compound is at least one selected from the group consisting of:

2-{4-[2-(4-chlorocinnamoylamino)-ethyl]phenoxy}-2-methylpropionic acid

2-{4-[2-(4-fluorocinnamoylamino)-ethyl]phenoxy}-2-methylpropionic acid

2-{4-[3-(4-chlorocinnamoylamino)-propyl]-phenoxy}2-methylpropionic acid

2-{4-[2-(3,4-dichlorocinnamoylamino)-ethyl]phenoxy}-2-methylpropionic acid

2-{{4-{2-[4-(4-chlorophenyl)-2,2-dimethylbutyroylamino]-ethyl}-phenoxy}}-2-methylpropionic acid.

* * * * *